United States Patent [19]

Fuchs et al.

[11] 4,405,793

[45] Sep. 20, 1983

[54] 1,3,4-OXADIAZOLES

[75] Inventors: Otto Fuchs, Frankfurt am Main; Klaus Hunger, Kelkheim; Dieter Weber, Kelkheim; Reinhard Zunker, Kelkheim, all of Fed. Rep. of Germany

[73] Assignee: Hoechst Aktiengesellschaft, Frankfurt am Main, Fed. Rep. of Germany

[21] Appl. No.: 8,394

[22] Filed: Feb. 1, 1979

Related U.S. Application Data

[63] Continuation of Ser. No. 865,490, Dec. 29, 1977, abandoned.

[30] Foreign Application Priority Data

Dec. 31, 1976 [DE] Fed. Rep. of Germany ....... 2659709

[51] Int. Cl.$^3$ .......................... C08K 5/23; C09B 35/34
[52] U.S. Cl. .................................... 548/131; 260/157; 564/149
[58] Field of Search .................... 260/307 G; 548/131

[56] References Cited

U.S. PATENT DOCUMENTS 2,973,358  2/1961  Pugin .......................... 260/307 G X

FOREIGN PATENT DOCUMENTS

| 929498 | 6/1955 | Fed. Rep. of Germany | ...... 260/157 |
| 49-69765 | 7/1974 | Japan | ..................... 260/157 |
| 51-68629 | 6/1976 | Japan | ..................... 260/157 |

*Primary Examiner*—Floyd D. Higel
*Attorney, Agent, or Firm*—Curtis, Morris & Safford

[57] ABSTRACT

2,5-Bis-(4'-aminophenyl)-1,3,4-oxadiazoles which are chlorinated in the phenyl nuclei are obtained by condensing hydrazine or a hydrazine yielding agent with equal or different chlorinated benzoic acids or acylating acid derivatives having in para-position to the acid group an amino group or a group capable of being transformed into the amino group, and, thereafter, effecting ring closure of the so-obtained bis-hydrazide to yield the oxadiazole. The products are bis-diazo components, especially for pigments having a very high tinctorial strength, clear and pure shades, a good fastness to light, to heat and to solvents.

3 Claims, No Drawings

1,3,4-OXADIAZOLES

This is a continuation of application Ser. No. 865,490 filed Dec. 29, 1977, now abandoned.

Subject of the present invention are 2,5-bis-[4'-aminophenyl]-1,3,4-oxadiazoles having general formula 1

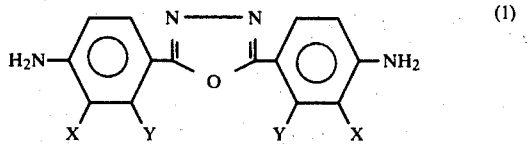

wherein one of the substituents X or Y is a hydrogen atom, the other one is a chlorine atom, as well as a process for preparing same, comprising the reaction of 2 mols of identical or different compounds of formula 2

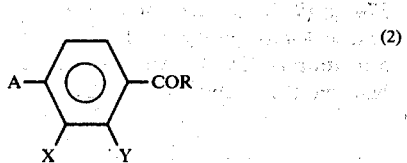

wherein A is the nitro group, the amino group, an alkanoyl amino group having 1 to 3 carbon atoms or a benzoyl amino group and R is the hydroxy group, a chlorine atom or a bromine atom or an alkoxy group having 1 to 4 carbon atoms, and X and Y have the meaning given in formula 1, with hydrazine or a compound that yields hydrazine under convenient conditions by a multistage or preferably one-stage process and, if A means the nitro group, the subsequent reduction, or, if A means an alkanoyl amino group or a benzoyl amino group, the hydrolysis.

Inorganic acids containing no or only a low amount of water such as concentrated phosphoric acid or concentrated sulfuric acid, preferably polyphosphoric acid or oleum (fuming sulfuric acid), are suitable media for a one-stage process, which comprises reacting 2 mols of the compound of formula 2 with 1 mol of hydrazine or of a compound that yields hydrazine, at temperatures of from 50° to 180° C.

When using polyphosphoric acid as reaction medium, there are reacted 2 mols of the compound of formula 2, A, R, X and Y having the above specified meaning, preferably however A meaning the nitro group and R representing the hydroxy group, with 1 mol of e.g. hydrazinium hydroxide or hydrazinium sulfate, at temperatures of from 50° to 180° C., preferably from 100° to 150° C. The corresponding oxadiazoles are obtained in a good yield, and if A is the nitro group with a practically quantitative yield, and at a high degree of purity. When oleum is used as reaction medium, there are reacted 2 mols of the compound of formula 2, A representing preferably the nitro group and R representing the hydroxy group, with 1 mol of hydrazinium sulfate at temperatures of from 50° to 130° C., preferably from 60° to 100° C. The corresponding oxadiazoles are obtained in good yields and purity degrees. They may be recrystallized from various solvents such as alcohols, nitrobenzene, dichlorobenzene or dimethyl formamide.

When the process is carried out as a multistage process, a bisacyl hydrazide is prepared directly or in two steps, depending on the substituent R, from the compounds 3 or 4 with hydrazine or with a compound that yields hydrazine. This bisacyl hydrazide is converted to the corresponding oxadiazole by heating with acid substances splitting off water, such as thionyl chloride, phosphorusoxychloride, phosphoruspentoxide, sulfuric acid, zinc chloride or carboxylic acid anhydrides. If R means an alkoxy group, a monoacyl hydrazide is formed that may be reacted with a further mol of the compound of formula 2 being an acid halide (R=halogen) to yield the bisacyl hydrazide. If R means a chlorine atom or bromine atom, the bisacyl hydrazide is formed directly. A has, in each case, the meaning specified for formula 2, the free amino group being less convenient.

The conversion of the nitro group to yield the amino group is carried out, for example, by catalytic hydrogenation with nickel catalysts or noble metal catalysts in aqueous or organic media or be reducing in a neutral or slightly acidic medium, e.g. in aqueous or alcoholic acetic acid, with metals such as iron, zinc or tin or with ionic reducing agents to produce practically quantitative yields.

An amino group protected by alkanoyl or benzoyl radicals, is set free by heating with dilute aqueous or alcoholic mineral acids.

The compound 2 (X=H, Y=Cl) may be obtained, for example, as 2-chloro-4-nitro-benzoic acid by oxidizing 2-chloro-4-nitrotoluene.

The compound 2 (X=Cl, Y=H) may also be obtained, for example as 3-chloro-4-nitro-benzoic acid from 3-chloro-4-nitro-aniline by exchanging the amino group (via the diazonium compound) for a nitrile group and by subjecting the nitrile group to hydrolysis or by oxidation of 3-chloro-4-nitro-toluene.

Subject of the invention is furthermore the use of the compounds of formula 1, as bisdiazo components for preparing disazo dyestuffs and especially disazo pigments. Disazo pigments may be obtained by bisdiazotizing the novel bisdiazo components according to known processes and by coupling them with ketomethylene compounds capable of enolization, such as acetoacetanilides, barbituric acid, or dihydroxy quinolines.

The disazo pigments prepared excel by very good tinctorial strength, clear color shades and good light fastness; they are as well highly resistant against the action of heat and solvents.

The following Examples illustrate the invention. Percentages are by weight unless otherwise stated.

EXAMPLE 1

65 g of hydrazinium sulfate are dissolved in 1000 g of polyphosphoric acid containing 84% of $P_2O_5$ at 80° C. under nitrogen cover. After having introduced 201.5 g of 3-chloro-4-nitrobenzoic acid, the mixture is agitated for one hour at 95°–100° C. and for further 5 hours at 145°–150° C. The solution cooled to 80° C. is then poured slowly into about 5 l of ice water. The precipitate is filtered off with suction, washed till neutral and dried. There are obtained 180 g of 2,5-bis-[3'-chloro-4'-nitrophenyl-(1')]-1,3,4-oxadiazole of formula 3, that melts at 236° C. after recrystallization from nitrobenzene.

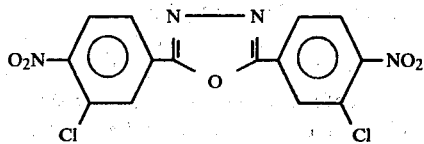

EXAMPLE 2

130 g of hydrazinium sulfate are dissolved in 2300 g of oleum containing 20% of free sulfur trioxide. There are added subsequently 403 g of 3-chloro-4-nitro-benzoic acid. The reaction mixture is heated to 65°–70° C. for 5 hours. It is allowed to cool, then poured onto ice. The precipitate is filtered off with suction, washed till neutral and dried. There are obtained 365 g of 2,5-bis-[3'-chloro-4'-nitrophenyl-(1')]-1,3,4-oxadiazole of formula 3, which melts at 236° C. after recrystallization from nitrobenzene.

EXAMPLE 3

101 g of 3-chloro-4-nitrobenzoic acid are introduced into 300 ml of thionyl chloride and 3 ml of dimethyl formamide. The mixture is agitated for one hour and a half at 50° C. and for 3 hours at 80° C. The excess of thionyl chloride is removed by distillation and the residue is dissolved in 600 ml of o-dichlorobenzene. At 50° C. there are added dropwise 20 g of 100% hydrazine hydrate and the mixture is agitated for 1 hour at 50° C. and for 2 hours at 100° C. After cooling, the product is filtered off with suction, washed and dried. There are obtained 90 g of bis-[3-chloro-4-nitrobenzoyl]-hydrazide of formula 4.

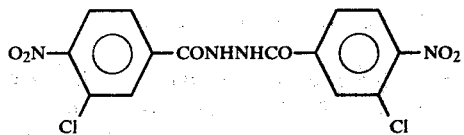

The product melts after recrystallization from n-butanol at 282° C.

Analysis: $C_{14}H_8Cl_2N_4O_6$: Calculated: C 42.1%; H 2.0%; Cl 17.8%; N 14.0%; O 24.0%; Found: C 42.4%; H 2.1%; Cl 17.5%; N 13.7%; O 23.8%

100 g of non-purified bis-[3-chloro-4-nitrobenzoyl]-hydrazide are heated in 400 ml of phosphorus oxychloride for 10 hours under reflux. The excess of phosphorus oxychloride is distilled off to a large extent. The residue is poured into ice water. The precipitate formed is filtered off with suction and washed to neutrality. There are obtained 76 g of 2,5-bis-[3'-chloro-4'-nitrophenyl-(1')]-1,3,4-oxadiazole of formula 3 which melts at 236° C. after recrystallization from nitrobenzene.

EXAMPLE 4

288 g of 2,5-bis-[3'-chloro-4'-nitrophenyl-(1')]-1,3,4-oxadiazole are suspended in 3200 ml of glacial acetic acid and 800 ml of water and then heated to 90° C. 250 g of iron powder are added in small portions within 70 minutes while stirring in such a way that the temperature can be maintained at 90°–95° C. Agitation is continued for 1 hour at a temperature of 90°–95° C. The cooled reaction mixture is poured into ice water. The precipitate is filtered off with suction and subsequently dissolved in hot dimethyl formamide. This solution is clarified over a kieselguhr layer. The filtrate is poured into ice water, the precipitate is filtered off with suction and washed with water. There are obtained 236 g of 2,5-bis-[4'-amino-3'-chlorophenyl-(1')]-1,3,4-oxadiazole of formula 1 (X=Cl, Y=H). The product melts at 306°–307° C. after recrystallization from o-dichlorobenzene.

Analysis: $C_{14}H_{10}Cl_2N_4O$: Calculated: C 52.34%; H 3.12%; Cl 22.12%; N 17.44%; O 4.98%; Found: C 52.2%; H 3.0%; Cl 21.7%; N 17.2%; O 5.0%

EXAMPLE 5

130 g of hydrazinium sulfate are dissolved in 2300 g of oleum containing 20% of free sulfur tiroxide. 403 g of 2-chloro-4-nitrobenzoic acid are introduced. The reaction mixture is stirred for 2 hours at 70° C. and for further 3 hours at 100° C. The solution then obtained is poured onto ice. The precipitate formed is filtered off with suction and washed till neutral. There are obtained 374 g (98% of the theoretical yield) of 2,5-bis-[2'-chloro-4'-nitrophenyl-(1')]-1,3,4-oxadiazole of formula 5 melting at 239° C. After recrystallization from nitrobenzene the melting point is 240° C.

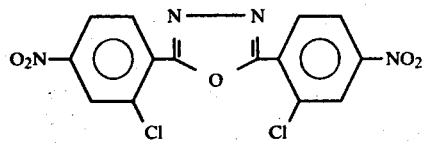

EXAMPLE 6

253 g of 2,5-bis-[2'-chloro-4'-nitrophenyl-(1')]-1,3,4-oxadiazole are heated to 80° C. in 3200 ml of ethanol and 800 ml of glacial acetic acid. 239 g of iron powder are added portionwise while stirring within 75 minutes in such a way that the mixture is boiling gently. Agitation is continued for 45 minutes under reflux, the mixture is then poured into about 6 l of ice water and the precipitate is filtered off with suction. The filter cake is briefly washed with water and then dissolved in warm dimethyl formamide. The solution is clarified over a kieselguhr layer. The filtrate is poured into water. The precipitate formed is filtered off with suction, washed and dried. There are obtained 202 g (95% of the theoretical yield) of 2,5-bis-[2'-chloro-4'-aminophenyl-(1')]-1,3,4-oxadiazole of formula 1 (X=H, Y=Cl) melting at 208° C.

Analysis: $C_{14}H_{10}Cl_2N_4O$: Calculated: C 52.34%; H 3.12%; Cl 22.12%; N 17.44%; O 4.98%; Found: C 52.5%; H 3.3%; Cl 22.0%; N 17.5%; O 5.0%

What is claimed is:

1. A compound of the formula (1)

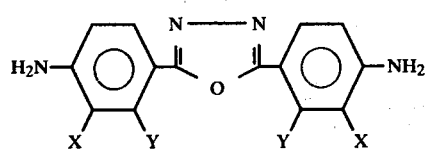

wherein one of the substituents X and Y is hydrogen and the other one is chlorine.

2. The compound as claimed in claim 1 having the formula

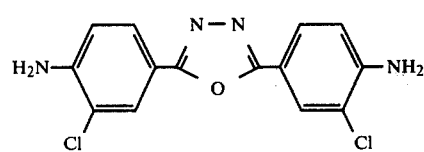
3. The compound as claimed in claim 1 having the formula
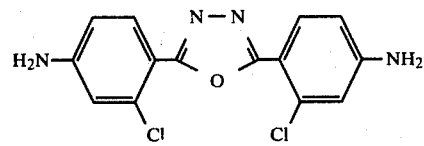
* * * * *